United States Patent [19]

Kokal, Jr.

[11] 3,959,881

[45] June 1, 1976

[54] BITE INTENSITY DETECTING ARTICULATING PAPER

[76] Inventor: August Kokal, Jr., 8710 Lone Star Road, Jacksonville, Fla. 32211

[22] Filed: Apr. 25, 1975

[21] Appl. No.: 571,691

[52] U.S. Cl. .................................................. 32/19
[51] Int. Cl.² .......................................... A61C 9/00
[58] Field of Search ........................................ 32/19

[56] References Cited
UNITED STATES PATENTS 3,813,781   6/1974   Forgione ................................ 32/19

*Primary Examiner*—Robert Peshock
*Attorney, Agent, or Firm*—Berman, Aisenberg & Platt

[57] ABSTRACT

A method and apparatus for marking tooth contact points in differing colors on occlusion. The differing colors correspond to differing biting pressures exerted between the teeth. The apparatus comprises paper impregnated with a plurality of groups of different color ink producing chemicals or individual granules, each of the different groups designed to rupture at different biting pressures for producing resultant various predetermined colors.

5 Claims, 3 Drawing Figures

BITE INTENSITY DETECTING ARTICULATING PAPER

BACKGROUND OF THE INVENTION

1. Field of the Invention

The present invention is related to dental articulation tests and, more particularly, to a method and apparatus for marking tooth contact points by means of which the location of premature contact points between upper and lower teeth may be determined.

2. Description of the Prior Art

Several methods and apparatuses are known for conducting dental articulation tests of the type described above. Prior art techniques include clamping a carbonized marking sheet between the teeth, and pressing the teeth into a relatively thick strip of wax or other impression-taking material. Deficiencies of such techniques include the lack of accurately definitive contact point locations sought to be determined.

In U.S. Pat. No. 3,421,223, Stark discloses an improvement upon such prior art techniques wherein substances which on intermixture produce a visible effect are applied separately to the occlusal surfaces of the upper and lower teeth. Upon occlusion these substances intermix to produce visible marks on the teeth at the points of contact. While generally representing an improvement over prior art techniques, I have found the Stark technique lacking any means to provide an indication of the relative biting pressures exerted by the upper and lower teeth upon one another. In other words, while the points of contact of the teeth may be more precisely determined, there is still no effective prior art apparatus or method by means of which the relative biting pressures between the occlusal surfaces may be quickly and accurately determined. Other prior U.S. patents of which I am aware include Shpuntoff (U.S. Pat. No. 3,604,116), Gravon (U.S. Pat. No. 3,686,761), Van Schaack (U.S. Pat. No. 3,734,081), and Faust et al. (U.S. Pat. No. 3,763,565). However, none of the latter provide any indication whatsoever of the relative biting pressures exerted by the occlusal surfaces of the upper and lower teeth.

OBJECTS AND SUMMARY OF THE INVENTION

It is therefore a primary object of the present invention to provide a novel and unique apparatus which enables the premature contact points on occlusion to be marked with a higher degree of precision than heretofore possible by providing an indication on the teeth of areas of greater and/or lesser biting pressures.

A further object of the present invention is to provide a marking technique which is straightforward and convenient in operation and which provides information far beyond that previously available by prior art dental articulation tests.

An additional object of the present invention is to provide apparatus for marking tooth contact points in differing colors on occlusion, the differing colors corresponding to differing biting pressures between the teeth, whereby more accurate information may be obtained such that the proper corrective measures may be more quickly and precisely determined.

The foregoing and other objects are achieved in accordance with one aspect of the present invention through the provision of an apparatus for marking tooth contact points in differing colors on occlusion. The differing colors correspond to differing biting pressures between the teeth. The tooth marking means comprises paper which is impregnated with a plurality of groups of minute ink producing chemicals or individual granules. Each of the groups of granules or chemicals contains a different color system of ink and is randomly dispersed through the paper. Further, the different groups of granules include means for rupturing at different biting pressures, whereby the appearance of certain colors on the teeth will correspond to the existence of a particular biting pressure, thereby providing a highly accurate indication of the relative biting pressures on occlusion. The means for intimate contact of catalyst and ink reactor chemical or physical rupturing at different biting pressures may comprise membranes of varying thicknesses disposed about the ink granules, different groups/colors of the granules having different thicknesses of membranes.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF A PREFERRED EMBODIMENT

Figure 1:
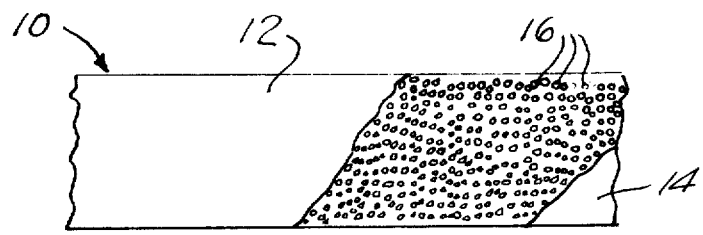
FIG. 1 is a plan view of the articulating paper according to a preferred embodiment of the present invention with portions broken away to show the construction thereof.

Referring now to the drawings, wherein like reference numerals designate identical or corresponding parts throughout the several views, and more particularly to FIG. 1 thereof, the articulating paper according to a preferred embodiment of the present invention is indicated generally by the reference numeral 10. Articulating paper 10 is seen to comprise an upper paper or mesh layer 12 and a lower paper or mesh layer 14, between which is interposed a plurality of miniscule ink granules 16.

Figure 2:
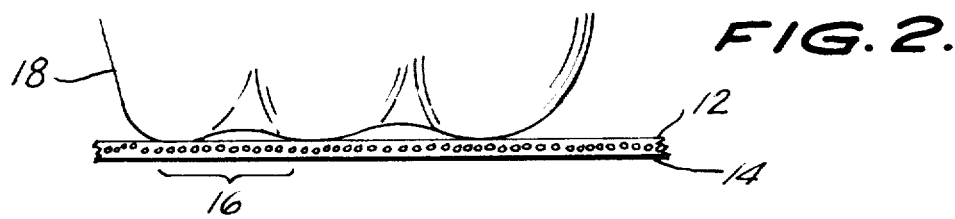
FIG. 2 is a side view of the articulating paper of FIG. 1 shown in cross section.

Impregnated ink granules 16 are comprised of a plurality of groups of ink granules, each of the groups having a different color ink or dye associated therewith. The ink granules 16 are packed at a very high density, the different groups of colors thereof being randomly interspersed in, for example, a single layer as seen in FIG. 2 or in numerous layers. Each of the ink granules 16 may be encased by a membrane, and the membranes utilized for different groups of colors preferably have different thicknesses so as to be rupturable at differing biting pressures. For example, groups of green ink granules may have a relatively thin membrane associated therewith which is designed to rupture in response to biting pressures in the range of 300–500 psi. Groups of red ink granules, for example, may have a medium thickness membrane associated therewith which is designed to rupture in response to biting pressures from 500–700 psi. Further, groups of blue granules, for example, may have a relatively thick membrane associated therewith which is designed to rupture in response to biting pressures in the range from 700–1000 psi. In this manner, upon occlusion, it would take relatively light tooth pressure to rupture the green ink granules, and a relatively large biting pressure to rupture the blue ink granules. As a result thereof and of the random dispersion of the differing color ink granules within the articulating paper 10, after occlusion the teeth will be marked with different colors, the user thereof then being able to detect the points of occlusion of greater and lesser biting pressures.

Figure 3:
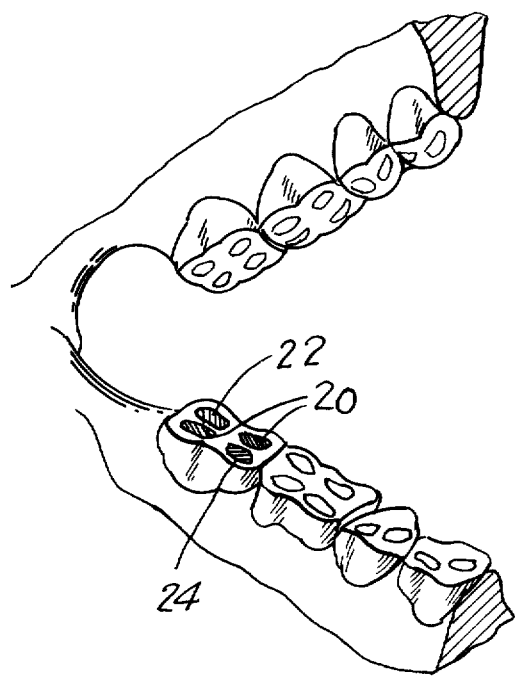
FIG. 3 is a perspective view showing the upper and lower teeth separated after using the apparatus according to the present invention.

This is seen more clearly with reference to FIG. 3, which illustrates a perspective view of the upper and lower teeth after utilization of the articulating paper of the present invention. The areas 20 indicate green ink spots, reference numeral 22 indicates a red ink spot, and reference numeral 24 indicates a blue ink spot. Clearly, to the user it will be apparent that point 24 is an area of a relatively large biting pressure compared to areas 22 or 20. Similarly, area 22 is indicative of a point of lesser biting pressure than area 24 but of a greater biting pressure than area 20, while area 20 indicates two points of minimum biting pressure. The foregoing, of course, holds true if the examples enunciated in the preceding paragraph are assumed. In this manner, a visual indication is provided not only of the precise contact points as in the prior art, but additionally of the relative biting pressure of the indicated contact points. The user is therefore provided with information not previously available with any degree of accuracy.

It should be apparent to a skilled technician that numerous modifications and variations of the present invention are possible in light of the above teachings. Obviously, the invention is not limited to the utilization of three color dyes or of this dye system, but any such number or system may be accommodated in accordance with the desired pressure differentiation. For example, rather than utilizing individual ink granules, a chemical and catalyst color producing system may be employed. Further, control could be achieved by varying the orientation of ink granules of different predetermined shapes and sizes. It is therefore to be understood that within the scope of the appended claims the invention may be practiced otherwise than as specifically described herein.

I claim:

1. Apparatus for marking tooth contact points in differing colors on occlusion, comprising:
   a. carrier means for insertion between the teeth;
   b. a plurality of rupturable marking means randomly dispersed in said carrier means for marking said contact points upon rupture, each of said marking means producing a different color; and
   c. means for causing each of said marking means to rupture at a different biting pressure.

2. The apparatus set forth in claim 1 wherein each of said marking means comprises a group of ink producing means, each of said groups of ink producing means producing ink of a different color.

3. The apparatus set forth in claim 2 wherein said means for causing each of said marking means to rupture at a different biting pressure comprises membrane means surrounding each of said groups of ink producing means, each of said groups of ink producing means being surrounded by membrane means of a different thickness.

4. The apparatus set forth in claim 3 wherein each of said groups of ink producing means comprises a group of ink granules, each of said ink granules within a group being surrounded by a membrane of the same thickness, but differing in thickness from the membranes sourrounding the ink granules in each of the other groups.

5. The apparatus set forth in claim 4 wherein said carrier comprises paper having an upper and a lower surface, said ink granules being randomly dispersed between said upper and lower surfaces.

* * * * *